United States Patent [19]

Christensen et al.

[11] 4,196,211
[45] Apr. 1, 1980

[54] 6-(α-HYDROXYETHYL)-7-OXO-1-AZABICY-CLO[3.2.0]HEPT-2-ENE-2-CARBOXYLIC ACID AND DERIVATIVES THEREOF

[75] Inventors: Burton G. Christensen, Metuchen; David H. Shih, Edison, both of N.J.

[73] Assignee: Merck & Co., Inc., Rahway, N.J.

[21] Appl. No.: 903,436

[22] Filed: May 8, 1978

Related U.S. Application Data

[63] Continuation-in-part of Ser. No. 847,297, Oct. 31, 1977, abandoned, which is a continuation-in-part of Ser. No. 668,898, Mar. 22, 1976, abandoned.

[51] Int. Cl.$^2$ .................. C07D 487/04; A61K 31/40
[52] U.S. Cl. ........................... 424/274; 260/245.2 R; 260/245.2 T; 260/326.2 R; 260/326.14 R; 260/326.25; 260/326.31; 544/239; 544/316; 544/353; 546/174; 546/275; 548/336
[58] Field of Search .................. 260/326.31; 424/274
[56] References Cited

U.S. PATENT DOCUMENTS 3,950,357  4/1976  Kahan et al. .................. 260/326.31

OTHER PUBLICATIONS

Fieser et al., Advanced Organic Chemistry; p. 310, (1961).
Wong et al., J.A.C.S. vol. 99, pp. 2823-2824, (1977).
Bose et al., J. Org. Chem. vol. 39, pp. 115-116, (1974).

*Primary Examiner*—Mary C. Lee
*Attorney, Agent, or Firm*—Rudolph J. Anderson, Jr.; Julian S. Levitt; Frank M. Mahon

[57] ABSTRACT

Disclosed are 6-(α-hydroxyethyl)-7-oxo-1-azabicyclo[3.2.0]hept-2-ene-2-carboxylic acid and its 2,3-dihydro analogue, 6-(α-hydroxyethyl)-7-oxo-1-azabicyclo[3.2.0]heptane-2-carboxylic acid. Such compounds and their pharmaceutically acceptable salt, ester, ether and aide derivatives (derivatives involving both the secondary alcohol and the carboxyl group) are useful as antibiotics. Also disclosed are processes for the preparation of such compounds, pharmaceutical compositions comprising such compounds and methods of treatment comprising administering such compounds and compositions when an antibiotic effect is indicated.

4 Claims, No Drawings

6-(α-HYDROXYETHYL)-7-OXO-1-AZABICY-CLO[3.2.0]HEPT-2-ENE-2-CARBOXYLIC ACID AND DERIVATIVES THEREOF

BACKGROUND OF THE INVENTION

This application is a continuation-in-part of U.S. application Ser. No. 847297, filed Oct. 31, 1977, which is a continuation-in-part of U.S. application Ser. No. 668,898, filed Mar. 22, 1976, both now abandoned.

This invention relates to 6-(α-hydroxyethyl)-7-oxo-1-azabicyclo[3.2.0]hept-2-ene-2-carboxylic acid, derivatives and the 2,3-dihydro analogues thereof which are useful as antibiotics. This invention also relates to processes for the preparation of such compounds; to pharmaceutical compositions comprising such compounds; and to methods of treatment comprising administering such compounds and compositions when an antibiotic effect is indicated.

The compounds of the present invention may be represented generically by the following structural formula (I):

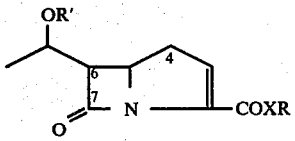

wherein R', X and R are independently selected from the groups hereinafter defined:
X is oxygen, sulphur or $NR^1$ ($R^1$ is hydrogen or R);
R is hydrogen, or inter alia, is representatively acceptable salt, ester and amide moieties known in the bicyclic β-lactam antibiotic art—such moieties are enumerated in greater detail below; and
R' is hydrogen; acyl (generically the group OR' is classifiable as an ester); or R' is selected from alkyl, aryl, aralkyl and the like (such that the group OR' is generically classifiable as an ether). The term "acyl" is by definition inclusive of the alkanoyls including derivatives and analogues thereof such as thio analogues wherein the carbonyl oxygen is replaced by sulphur; as well as sulphur and phosphorous acyl analogues such as substituted sulfonyl-, sulfinyl-, and sulfenyl radicals, and substituted phosphorous-, phosphoric-, phosphonous- and phosphonic radicals. Such radicals, R', of the present invention are enumerated in greater detail below.

The compounds of the present invention, I are related to the new antibiotic Thienamycin. Thienamycin is known to have the following structural formula (II):

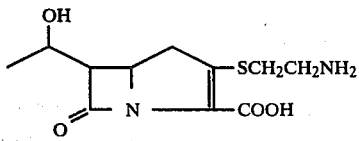

Thienamycin is disclosed and claimed in co-pending, commonly assigned U.S. Patent Application Ser. No. 526,992, filed Nov. 25, 1974 (Now U.S. Pat. No. 3,950,357, Apr. 13, 1976). The identified application is incorporated herein by reference since Thienamycin may serve as the starting material for the preparation of the compounds of the present invention through removal of the 3-aminoethylthio side chain of Thienamycin.

Thienamycin and all of its isomers (in pure form and as mixtures) are also obtainable by the total synthesis disclosed and claimed in co-pending, commonly assigned U.S. Patent Application Ser. No. 833,210 (Sept. 15, 1977), now abandoned. This applicaton is incorporated herein by reference to the extent that it makes available all isomers of II as starting materials in the preparation of the compounds of the present invention (I).

There is a continuing need for new antibiotics. For unfortunately, there is no static effectiveness of a given antibiotic selectively gives rise to resistant strains of pathogens. In addition, the known antibiotics suffer from the disadvantage of being effective only against certain types of microorganisms. Accordingly, the search for new antibiotics continues.

Unexpectedly, it has been found that the compounds of the present invention are broad spectrum antibiotics, which are useful in animal and human therapy and in inanimate systems.

Thus, it is an object of the present invention to provide a novel class of antibiotics which possess the basic nuclear structure, I, given above. These antibiotics are active against a broad range of pathogens which representatively include both gram positive bacteria such as *S. aureus, S. pyrogenes* and *B. subtilis* and gram negative bacteria such as *E. coli., Proteus morganii, Klebsiella* and *Pseudomonas.* Further objects of this invention are to provide chemical processes for the preparation of such antibiotics and their non-toxic pharmaceutically acceptable salt, ester and amide derivatives; pharmaceutical compositions comprising such antibiotics; and to provide methods of treatment comprising administering such antibiotics and compositions when an antibiotic effect is indicated.

DETAILED DESCRIPTION OF THE INVENTION

I. Identification of Radicals R, X and R':

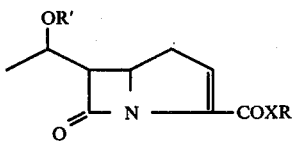

In the generic description of the invention (I, above), the radical COXR symbolizes in addition to the free carboxyl group (X is oxygen and R is hydrogen) the pharmaceutically acceptable salt, ester and amide derivatives of the free acid. Thus, X is selected from the group consisting of oxygen, sulfur, and $NR^1$ ($R^1$ is hydrogen or R); and R is selected from the group consisting of hydrogen, alkyl having 1-10 carbon atoms, straight or branched, such as methyl, ethyl, t-butyl, pentyl, decyl, and the like; carbonylmethyl, including phenacyl, p-bromophenacyl, p-t-butylphenacyl, acetoxyacetylmethyl, pivaloxyacetylmethyl, carboxymethyl and its alkyl and aryl esters, α-moiety has 1-10 and preferably 1-6 carbon atoms, but can be branched, straight, or cyclic, and the alkyl moiety has 1-6 carbon atoms, such as methoxymethyl, ethoxymethyl, isopropoxymethyl, decyloxymethyl, ethoxypropyl, decyloxypentyl, cyclohexyloxymethyl and the like; alkanoyloxyalkyl wherein the alkanoyloxy moiety is straight or branched and has 1-6 carbon atoms and the alkyl portion has 1-6 carbon atoms, such as acetoxymethyl, pivaloyloxymethyl, acetoxyethyl, propionyloxyethyl, acetoxypropyl, and the like; acylthioalkyl, e.g., acetylthiomethyl, acetylthioethyl, pivaloylthiomethyl and the like; haloalkyl wherein halo is chloro, bromo, fluoro or iodo and the alkyl portion is straight or branched having 1-6 carbon atoms, e.g., 2,2,2-trichloroethyl, trifluoroethyl, 2-bromopropyl, diiodomethyl, 2-chloroethyl, 2-bromoethyl, and the like; alkenyl having 2-10 carbon atoms, either straight or branched, e.g., allyl, 3-butenyl, 4-butenyl, 4-pentenyl, 2-butenyl, 3-pentenyl, 3-methyl-2-butenyl, 2-methyl-2-propenyl, 1,4-cyclohexadien-1-methyl, and the like; alkynyl having 2-10 carbon atoms, either straight or branched, e.g., 3-pentynyl, propargyl, ethynyl, 3-butyn-1-yl, and the like; alkanoyl, either straight or branched, having 1-10 carbon atoms, such as pivaloyl, acetyl, propionyl, and the like; aralkyl or heteroaralkyl wherein alkyl has 1-3 carbon atoms, and hetero means 1-4 hetero atoms being selected from the group consisting of O, S, or N, such as benzyl, benzhydryl, and substituted benzyl, benzhydryl, or e.g., benzyl or benzhydryl substituted with 1-3 substituents such as benzyl, phenoxy, halo, loweralkyl, loweralkanoyloxy of 1-5 carbon atoms, lower alkoxy, hydroxy, nitro, blocked carboxy, or combinations thereof, e.g., p-chlorobenzyl, o-nitrobenzyl, 3,5-dinitrobenzyl, p-methoxybenzyl, m-benzoylbenzyl, p-t-butylbenzyl, m-phenoxybenzyl, p-benzoylbenzyl, p-nitrobenzyl, 3,5-dichloro-4-hydroxybenzyl, p-methoxycarbonylbenzyl, p-methoxybenzhydryl, p-carboxybenzyl, the latter being either the free acid, ester or the sodium salt, 2,4,6-trimethylbenzyl, p-pivaloyloxybenzyl, p-t-butyoxycarbonyl benzyl, p-methylbenzyl, p-benzoyloxybenzyl, p-acetoxybenzyl, p-2-ethylhexanoylbenzoyl, p-ethoxycarbonylbenzyl, p-benzoylthiobenzyl, p-benzamidobenzyl, o-pivaloxyloxybenzyl, m-pivaloyloxybenzyl, p-isopropoxybenzyl, p-t-butoxybenzyl, as well as cyclic analogues thereof, 2,2-dimethyl-5-coumaranmethyl, 5-indanylmethyl, p-trimethylsilylbenzyl, 3,5-bis-t-butyoxy-4-hydroxybenzyl; 2-thienylmethyl, 2-furylmethyl, 3-t-butyl-5-isothiazolmethyl, 6-pivaloyloxy-3-pyridazinemethyl, 5-phenylthio-1-tetrazolylmethyl, or the like) the use of the terms lower alkyl or lower alkoxy in this context means 1-4 carbon atom chain); or phthalidyl; or phenylethyl, 2-(p-methylphenyl)-ethyl, and the arylthioalkyl analogues, aryloxyalkyl wherein aryl is preferably a phenyl ring having 0-3 substituents, preferably 0 or 1 substituents in the ortho or para positions and alkyl is 1-6 carbon atoms, e.g., (4-methoxy)phenoxymethyl, phenoxymethyl, (4-chloro)phenoxymethyl, (4-nitro)phenoxymethyl, (4-benzyloxy)phenoxymethyl, (4-methyl)phenoxymethyl, (4-benzyloxy)phenoxymethyl, (4-methyl)phenoxymethyl, (2-methoxy)phenoxymethyl, (1-phenoxy)-ethyl, (4-amino)phenoxymethy, (4-methoxy)phenylthiomethyl, (4-chloro)phenylthiomethyl, phenylthioethyl; aryl wherein aryl is phenyl, 5-indanyl, or substituted phenyl having 0-3 substituents, preferably 0 or 1 substitutent in the ortho or para position, e.g., (4-methyl)-phenyl, (4-hydroxy)-phenyl, (4-t-butyl)phenyl, p-nitrophenyl, 3,5-dinitrophenyl, or p-carboxyphenyl, the latter having either the free acid or the sodium salt form; aralkenyl wherein aryl is phenyl and the alkenyl has 1-6 carbon atoms, such as 3-phenyl-2-propenyl; aralkoxyalkyl wherein aralkoxy is benzyloxy, and alkyl has 1-3 carbon atoms, such as benzyloxymethyl, (4-nitro)benzyloxymethyl, (4-chloro)benzyloxymethyl;

alkylthioalkyl wherein the alkylthio portion has 1-10 and preferably 1-6 carbon atoms, but can be branched, straight, or cyclic, and the alkyl portion has 1-6 carbon atoms, such as methylthioethyl, ethylthioethyl, cyclohexylthiomethyl, decylthiobutyl, methylthiopropyl, isopropylthioethyl, methylthiobutyl and the like.

In addition to the esters (and thio esters) listed above, amides are also embraced by the present invention, i.e., wherein X is the

group. Representative of such amides, —CONR$^1$R are those wherein R$^1$ is selected from the group consisting of hydrogen, methyl, ethyl, phenyl, p-methoxyphenyl, benzyl, carboxymethyl, methylthioethyl and heteroaryl; also embraced by —COXR are anhydrides wherein R is acyl (the term "acyl" is defined for purposes of the present invention below) such as benzyloxycarbonyl, ethoxycarbonyl, benzoyl, and pivaloyl.

Particularly preferred esters are those wherein X is oxygen and R is aralkyl, aryloxyalkyl, aralkoxyalkyl, alkylthioalkyl, haloalkyl and alkenyl.

The most preferred COXR-bearing compounds of the present invention are those wherein (relative to structure I, above) X is oxygen, sulphur or NR$^1$ (R$^1$ is selected from the group consisting of hydrogen and lower alkyl); and R is selected from the group consisting of: alkyl alkenyl, such as 2-methyl-2-propenyl,3-methylbu-2-tenyl, 3-butenyl and the like; methylthio ethyl; benzyl and substituted benzyl, such as p-t-butylbenzyl, m-phenoxybenzyl, p-pivaloyloxybenzyl, p-nitrobenzyl and the like; pivaloyloxymethyl, 3-phthalidyl, acetoxymethyl, acylthioalkyl such as acetylthiomethyl, acetylthioethyl, pivaloylthiomethyl and the like.

Critical to the definition of R' (below) and R (above) in the generic description of the present invention (structure I, above) is the definition of the term "acyl". Thus, the acyl radical represented by either R or R' can be substituted or unsubstituted aliphatic, aromatic or heterocyclic, araliphatic or heterocylyaliphatic carboxylic acid radical, a substituted or unsubstituted carbamoyl radical or a carbothioic acid radical. One group of acyl radicals can be represented by the general formula:

wherein X is O or S and R'' represents hydrogen; amino; substituted amino such as alkyl- and dialkylamino wherein the alkyl radical comprises 1 to about 6 carbon atoms; substituted or unsubstituted straight or branched chain alkyl wherein the alkyl radical comprises 1 to about 6 carbon atoms; mercapto such as alkylthio, typically comprising 1 to 6 carbon atoms; hydroxy such as alkoxy, typically comprising 1 to 6 carbon atoms; aryloxy, typically comprising 6 to 10 carbon atoms; alkenyl, or alkynyl groups typically comprising 2 to 6 carbon atoms; aryl such as phenyl; aralkyl such as benzyl; cycloalkyl, typically comprising 3 to 6 carbon atoms; or a heteroaryl or heteroaralkyl group (mono- and bicyclic) wherein the alkyl moiety typically comprises 1 to 3 carbon atoms and the heterocyclic ring comprises typically 4-10 atoms and the hetero atom or atoms are selected from O, N and S; such groups can be unsubstituted or can be substituted by radicals such as OH, SH, SR (R is loweralkyl or aryl such as phenyl), alkyl or alkoxy groups having 1 to about 6 carbon atoms, halo, such as Cl, Br, F and I, cyano, carboxy, sulfamino, carbamoyl, sulfonyl, azido, amino, substituted amino such as alkylamino including quaternary ammonium wherein the alkyl group comprises 1 to 6 carbon atoms, haloalkyl such as trifluoromethyl, carboxyalkyl, carbamoylalkyl, N-substituted carbamoylalkyl, wherein the alkyl moiety of the foregoing three radicals comprises 1 to about 6 carbon atoms, amidino, guanidino, N-substituted guanidino, guanidino lower alkyl and the like. Representative examples of such acyl groups that might be mentioned are those wherein R" is benzyl, p-hydroxybenzyl, 4-amino-4-carboxybutyl, methyl, cyanomethyl, 2-pentenyl, n-amyl, n-heptyl, ethyl, 3- or 4-nitrobenzyl, phenethyl, β,β-diphenylethyl, methyldiphenylmethyl, triphenylmethyl, 2-methoxyphenyl, 2,6-dimethoxyphenyl, 2,4,6-trimethoxyphenyl, 3,5-dimethyl-4-isoxazolyl, 3-butyl-5-methyl-4-isoxazolyl, 5-methyl-3-phenyl-4-isoxazolyl, 3-(2-chlorophenyl)-5-methyl-4-isoxazolyl, 3-(2,6-dichlorophenyl)5-methyl-4-isoxazolyl, D-4-amino-4-carboxybutyl, D-4-N-benzoylamino-4-carboxy-n-butyl, p-aminobenzyl, o-aminobenzyl, m-aminobenzyl, p-dimethylaminobenzyl, (3-pyridyl)methyl, 2-ethoxy-1-naphthyl, 3-carboxy-2-quinoxalinyl, 3-(2,6-dichlorophenyl)-5-(2-furyl)-4-isoxazolyl, 3-phenyl-4-isoxazolyl, 5-methyl-3-(4-guanidinophenyl)-4-isoxazolyl, 4-guanidinomethylphenyl, 4-guanidinomethylbenzyl, 4-guanidinobenzyl, 4-guanidinophenyl, 2,6-dimethoxy-4-guanidino, o-sulfobenzyl, p-carboxymethylbenzyl, p-carbamoylmethylbenzyl, m-fluorobenzyl, m-bromobenzyl, p-chlorobenzyl, p-methoxybenzyl, 1-naphthylmethyl, 3-isothiazolylmethyl, 4-isothiazolylmethyl, 5-isothiazolylmethyl, guanylthiomethyl, 4-pyridylmethyl, 5-iosxazolylmethyl, 4-methoxy-5-isoxazolylmethyl, 4-methyl-5-isoxazolylmethyl, 1-imidazolylmethyl, 2-benzofuranylmethyl, 2-indolylmethyl, 2-phenylvinyl, 2-phenylethynyl, 1-aminocyclohexyl, 2- and 3-thienylaminomethyl, 2-(5-nitrofuranyl)vinyl, phenyl, o-methoxyphenyl, o-chlorophenyl, o-phenylphenyl, p-aminomethylbenzyl, 1-(5-cyanotriazolyl)methyl, difluoromethyl, dichloromethyl, dibromomethyl, 1-(3-methylimidazolyl)methyl, 2- or 3-(5-carboxymethylthienyl)methyl, 2- or 3-(4-carbamoylthienyl)-methyl, 2- or 3-(5-methylthienyl)methyl, 2- or 3-(methoxythienyl)-methyl, 2- or 3-(4-chlorothienyl)-methyl,2- or 3-(5-sulfothienyl)methyl, 2- or 3-(5-carboxythienyl)methyl, 3-(1,2,5-thiadiazolyl)methyl, 3-(4-methoxy-1,2,5-thiadiazolyl) methyl, 2-furylmethyl, 2-(5-nitrofuryl)-methyl, 3-furylmethyl, 2-thienylmethyl, 3-thienylmethyl, tetrazolylmethyl benzamidinomethyl and cyclohexylamidinomethyl The acyl group can also be a radical of the formula

wherein X is O or S and n is 0–4, Z represents oxygen, sulfur, carbonyl or nitrogen and R" is defined as above. Representative members of the substituent

that might be mentioned are allylthiomethyl, phenylthiomethyl, butylmercaptomethyl, α-chlorocrotylmercaptomethyl, phenoxymethyl, phenoxyethyl, phenoxybutyl, phenoxybenzyl, diphenoxymethyl, dimethylmethoxymethyl, dimethylbutoxymethyl, dimethylphenoxymethyl, 4-guanidinophenoxymethyl, 4-pyridylthiomethyl, p-(carboxymethyl)phenoxymethyl, p-(carboxymethyl)-phenylthiomethyl, 2-thiazolylthiomethyl, p-(sulfo)phenoxymethyl, p-(carboxymethyl)phenylthiomethyl, 2-pyrimidinylthiomethyl, phenethylthiomethyl, 1-(5,6,7,8-tetrahydronaphthyl)oxomethyl, N-methyl-4-pyridylthio, benzyloxy, methoxy, ethoxy, phenoxy, phenylthio, amino, methylamino, dimethylamino, pyridinium methyl, trimethylammoniummethyl, cyanomethylthiomethyl, trifluoromethylthiomethyl, 4-pyridylethyl, 4-pyridylpropyl, 4-pyridylbutyl, 3-imidazolylethyl, 3-imidazolylpropyl, 3-imidazolylbutyl, 1-pyrroloethyl, 1-pyrrolopropyl and 1-pyrrolobutyl.

Alternatively, the acyl group can be a radical of the formula:

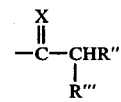

wherein R" is defined as above and R''' is a radical such as amino, hydroxy, azido, carbamoyl, guanidino, acyloxy, halo, such as Cl, F, Br, I, sulfamino, tetrazolyl, sulfo carboxy, carbalkoxy, phosphono and the like.

Represnetative members of the substituent

that might be mentioned are α-aminobenzyl, α-amino-(2-thienyl)methyl, α-(methylamino)benzyl, α-aminomethylmercaptopropyl, α-amino-3- or 4-chlorobenzyl, α-amino-3 or 4-hydroxybenzyl, α-amino-2,4-dichlorobenzyl, α-amino-3,4-dichlorobenzyl, D(—)-α-hydroxybenzyl, α-carboxybenzyl, α-amino-(3-thienyl)methyl D-(—)-α-amino-3-chloro-4-hydroxybenzyl, α-amino-(cyclohexyl)methyl, α-(5-tetrazolyl)-benzyl, 2-thienylcarboxymethyl, 3-thienyl-carboxymethyl, 2-furylcarboxymethyl, 3-furyl-carboxymethyl, α-sulfaminobenzyl, 3-thienyl-sulfaminomethyl, α-(N-methylsulfamino)-benzyl, D(—)-2-thienyl-guanidinomethyl, D(—)-α-guanidinobenzyl, α-guanylureidobenzyl, α-hydroxybenzyl, α-azidobenzyl, α-fluorobenzyl, 4-(5-methoxy-1,3-oxadiazolyl)-aminomethyl, 4-(5-methoxy-1,3-oxadiazolyl)-hydroxymethyl, 4-(5-methoxy-1,3-sulfadiazolyl)-hydroxymethyl, 4-(5-chlorothienyl)-aminomethyl, 2-(5-chlorothienyl)-hydroxymethyl, 2-(5-chlorothienyl)-carboxy-methyl, 3-(1,2-thiazolyl)-aminomethyl, 3-(1,2-thiazolyl)-hydroxymethyl, 3-(1,2-thiazolyl)-carboxymethyl, 2-(1,4-thiazolyl)-aminomethyl, 2-(1,4-thiazolyl)-hydroxymethyl,2-(1,4-thiazolyl)-carboxymethyl, 2-benzothienylaminomethyl, 2-benzothienylhydroxymethyl, 2-benzothienylcarboxymethyl, α-sulfobenzyl, α-phosphonobenzyl, α-diethylphosphono and α-monoethylphosphono.

The acyl substituent $R^1$ and $R^2$ may also be selected from the sulphur (I) and phosphorous (II) radicals:

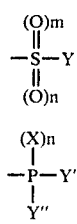

$$\begin{array}{c}(O)_m\\\|\\-S-Y\\\|\\(O)_n\end{array} \quad (I)$$

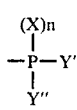

$$\begin{array}{c}(X)_n\\|\\-P-Y'\\|\\Y''\end{array} \quad (II)$$

wherein with respect to I, m and n are integers selected from 0 or 1 and $Y = O^\ominus M^\oplus$, $-N(R'')_2$ and $R''$ wherein $M^\oplus$ is selected from hydrogen, alkali metal cations and organic bases; and $R''$ is as defined above, e.g., alkyl, alkenyl, aryl and heteroaryl. With respect to II, $X = O$ or S; $n = 0$ or 1; and $Y'$ and $Y''$ are selected from the group consisting of $O^\ominus M^\oplus$, $-N(R'')_2$, $R''$ and $ZR''$ wherein all symbolism is as defined above, e.g., $R''$ and $ZR''$ are representatively: alkyl, alkenyl, aryl, heteroaryloxy; $Y'$ and $Y''$, including $R''$ moieties, can be joined together to form cyclic ester, ester-amide and amide functions. Illustrative examples of (I) are N-(methylsulphonyl)-thienamycin, N-(o-nitrophenylsulphonyl)thienamycin, N-(p-chlorophenylsulphinyl)-thienamycin, N-(o-nitrophenylsulphenyl)thienamycin, N-sulphamoylthienamycin, N-dimethylsulphamoyl-thienamycin and thienamycin N-sulphonic acid sodium salt. Illustrative examples of (II) are N-(dimethoxyphosphino)thienamycin, N-(dibenzyloxyphosphino)-thienamycin, N-(dihydroxyphosphino)thienamycin disodium salt, N-(dimethoxyphosphinyl)thienamycin, N-(dimethoxyphosphinothioyl)thienamycin, N-(dibenzyloxyphosphinyl)-thienamycin, N-(dihydroxyphosphinyl)-thienamycin disodium salt.

The acyl substituents of the general formula

$$\begin{array}{c}O\\\|\\-CCHR^3R^4\end{array}$$

wherein $R^3$ and $R^4$ are as defined below represent a preferred group of substituents. $R^3$ represents hydrogen, halo, such as chloro, fluoro, bromo, iodo, amino, guanidino, phosphono, hydroxy, tetrazolyl, carboxy, sulfo, or sulfamino and $R^4$ represents phenyl, substituted phenyl, a mono- or bicyclic heterocycle containing one or more oxygen, sulfur or nitrogen atoms in the ring, such as furyl, quinoxalyl, thienyl, quinolyl, quinazolyl, thiazolyl, isothiazolyl, tetrazolyl, oxadiazolyl, thiadiazolyl and the like substituted heterocycles, phenylthio, phenyloxy, lower alkyl of 1–6 carbon atoms, heterocyclic or substituted heterocyclic thio groups; or cyano. The substituents on the radicals can be halo, carboxymethyl, guanidino, guanidinomethyl, carboxamidomethyl, aminomethyl, nitro, methoxy or methyl.

Particularly preferred acyl groups are those wherein $R^3$ is selected from the group consisting of hydrogen, hydroxy, amino or carboxy and $R^4$ is selected from the group consisting of phenyl, or a 5- or 6-membered heterocyclic ring having one or two sulfur, oxygen or nitrogen heteroatom atoms, such as tetrazolyl, thienyl, furyl and phenyl.

Examples of acyl radicals of interest are phenylacetyl, 3-bromophenylacetyl, p-aminomethylphenylacetyl, 4-carboxymethylphenylacetyl, 4-carboxyamidomethylphenylacetyl, 2-furylacetyl, 5-nitro-2-furylacetyl, 3-furylacetyl, 2-thienylacetyl, 5-chloro-2-thienylacetyl, 5-methoxy-2-thienylacetyl, α-guanidino-2-thienylacetyl, 3-thienylacetyl, 2-(4-methylthienyl)acetyl, 3-isothiazolylacetyl, 4-methoxy-3-isothiazolylacetyl, 4-isothiazolylacetyl, 3-methyl-4-isothiazolylacetyl, 5-isothiazolylacetyl, 3-chloro-5-isothiazolylacetyl, 3-methyl-1,2,5-oxadiazolylacetyl, 1,2,5-thiadiazolyl-4-acetyl, 3-methyl-1,2,5-thiadiazolylacetyl, 3-chloro-1,2,5-thiadiazolylacetyl, 3-methoxy-1,2,5-thiadiazolylacetyl, phenylthioacetyl, 4-pyridylthioacetyl, cyanoacetyl, 1-tetrazolylacetyl, α-fluorophenylacetyl, D-phenylglycyl, 4-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-amino cyclohexadienylacetyl, α-sulfaminophenylacetyl, α-hydroxyphenylacetyl, α-tetrazolylphenylacetyl and α-sulfophenylacetyl.

Further with regard to the generic description of the compounds of the present invention (I, above), $R'$ is hydrogen, or the group $-OR'$ is classifiable as an ester or ether; in the ester embodiment, $R'$ is defined by the acyl group given above; in the ether embodiment, $R'$ is selected from the radicals: $R''$, $-(CH_2)_nZR''$, $-CHR''R'''$ and $-CHR^3R^4$, all of which have been defined in the definition of "acyl", above.

It should be noted that embodiments of the present invention wherein $R'$ is other than hydrogen and $-COXR$ is $-COOH$ (the free acid) are prepared by selective deblocking of the carboxyl group such as by hydrolysis or hydrogenation after derivatization of the alcoholic group (establishment of $R'$, structure I, above). Particularly suitable ester radicals, R, for this purpose when $X = O$ are substituted and unsubstituted benzyl such as p-nitrobenzyl.

Suitable blocking esters also include those selected from the following list which is representative and not intended to be an exhaustive list of possible ester groups, wherein $X = O$ and R is given:

(i) $R = CR^aR^bR^c$ wherein at least one of $R^a$, $R^b$, and $R^c$ is an electron-donor e.g., p-methoxyphenyl, 2,4,6-trimethylphenyl, 9-anthryl, methoxy, $CH_2SCH_3$, tetrahydrofur-2-yl, tetrahydropyran-2-yl, or fur-2-yl. The remaining $R^a$, $R^b$ and $R^c$ groups may be hydrogen or organic substituting groups. Suitable ester groups of this type include p-methoxybenzyloxycarbonyl and 2,4,6-trimethylbenzyloxycarbonyl.

(ii) $R = CR^aR^bR^c$ wherein at least one or $R^a$, $R^b$, and $R^c$ is an electron-attracting group, e.g., benzoyl, p-nitrophenyl, 4-pyridyl, trichloromethyl, tribromomethyl, iodomethyl, cyanomethyl, ethoxycarbonylmethyl, arylsulphonylmethyl, 2-dimethylsulphoniumethyl, o-nitrophenyl or cyano. Suitable esters of this type include benzoylmethoxycarbonyl, p-nitrobenzyloxycarbonyl, 4-pyridylmethoxycarbonyl, 2,2,2-trichloroethoxycarbonyl and 2,2,2-tribromoethoxycarbonyl.

(iii) $R = CR^aR^bR^c$ wherein at least two of $R^a$, $R^b$ and $R^c$ are hydrocarbon such as alkyl, e.g. methyl or ethyl, or aryl e.g. phenyl and the remaining $R^a$, $R^b$ and $R^c$ group, if there is one, is hydrogen. Suitable esters of this type include t-butyloxycarbonyl, t-amyloxycarbonyl, diphenylmethoxycarbonyl and triphenylmethoxycarbonyl.

(iv) $R = R^d$, wherein $R^d$ is adamantyl, 2-benzyloxyphenyl, 4-methylthiophenyl or tetrahydropyran-2-yl.

Silyl esters, under this category of blocking groups, may conveniently be prepared from a halosilane or a silazane of the formula $R^4{}_3SiX'$; $R^4{}_2SiX'{}_2$; $R^4{}_3Si.NR^4{}_2$; $R^4{}_3Si.NH.COR^4$; $R^4{}_3Si.NH.CO.NH.SiR^4{}_3$; $R^4NH.CO.NR^4.SiR^4{}_3$; or $R^4C(OSiR^4{}_3)$;

$HN(SiR^4{}_3)_2$ wherein X' is a halogen such as chloro or bromo and the various groups $R^4$, which can be the same or different, represent hydrogen atoms or alkyl, e.g. methyl, ethyl, n-propyl iso-propyl; arly, e.g. phenyl; or aralkyl, e.g. benzyl groups.

In this connection, it is noted that preferred R "blocking groups" include the sub-generic groups defined above as aralkyl, haloalkyl, alkanoyloxyalkyl, alkoxyalkyl, alkenyl, substituted alkyl, or aralkoxyalkyl, and also including alkylsilyl, wherein alkyl has 1–10 carbon atoms.

More specifically, preferred R "blocking groups" including benzyl, phenacyl, p-nitrobenzyl, methoxymethyl, trichloroethyl, trimethylsilyl, tributyltin, p-methoxybenzyl, benzhydryl. These blocking groups are preferred since they are generally recognized as easily-removable blocking groups in the related antibiotic, bicyclic β-lactam art.

II. Preparation

The compounds of the present invention are conveniently prepared by the hydrogenation of Thienamycin (II, above) or a derivative thereof according to the following reaction:

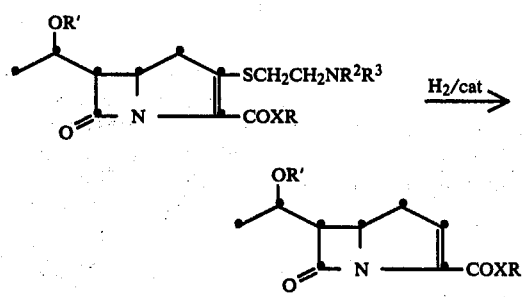

wherein R', X and R are as defined above, and $R^2$ and $R^3$ are independently selected from hydrogen or acyl.

Preferably, in the above reaction scheme the starting material is an N-acylated thienamycin derivative wherein the acyl moiety comprises an aromatic ring such as N-phenoxyacetyl thienamycin:

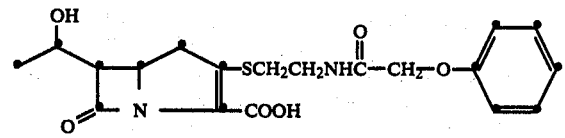

Such N-acylated thienamycin species wherein the acyl moiety comprises an aromatic ring are preferred in the preparation of the compounds of the present invention since it is convenient to isolate the desired product (I) after hydrogenolysis by chromatographic resolution of the reaction mixture on a polystyrene resin which has an affinity for the aromatic nucleus carried by the cleaved cysteaminyl side chain but little or no affinity for the decysteaminyl thienamycin derivatives of the present invention.

Suitable catalysts for the above hydrogenation reaction include the platinum metals and oxides thereof such as palladium, platium, rhodium and the like and Raney nickel for example. Preferably, as mentioned above, the thienamycin substrate is an N-acylated thienamycin derivative wherein the acyl moiety comprises an aromatic ring. Preferably, the hydrogenation reaction is conducted in a hydrogenation flask wherein the thienamycin substrate to be reduced is dissolved in water or an aqueous mixture of water and a polar organic solvent such as dioxane, tetrahydrofuran, dimethylformamide (DMF) or the like. The product, I, is obtained in essentially quantitative yield on hydrogenation as described above at from 0° to 50° C., under from 1 to 2 atmospheres of hydrogen for from 0.5 to 3 hours.

As mentioned above, the desired product of the above hydrogenation scheme is separated from its starting material and from the cysteaminyl residue by chromatographic separation on a polystyrene resin such as XAD-2 resin (obtained from the Rohm & Haas Company). Typically, the separation procedure is conducted by charging the reaction volume onto a column of XAD-2 resin, followed by elution with water. Identification of the desired fractions is made by monitoring labelled fractions by ultra-violet absorption and high pressure liquid chromatography, HPLC (Water Associates). Because of the affinity for the XAD-2 resin for the aromatic acyl moiety, the separation of the products of the present invention is easily effected from the starting material and from by-products of the hydrogenolysis. Typically, evaluation of the fractions off the XAD-2 resin is carried out by injecting a sample aliquot (1 μl) of the fraction in question into the HPLC system which is equipped with a 254 nm uv detector and a 2 ft.×⅛ inch i.d. column packed with $C_{18}$ Bondapak reverse phase adsorbent (supplied by Waters Associates). The column is eluted with a 10% tetrahydrofuran (THF) aqueous solution at a flow rate of 0.5 ml./min.

Embodiments of the invention wherein R' is other than hydrogen and/or —XR is other than —OH, may be obtained as above illustrated by performing the hydrogenolysis and reduction upon the corresponding thienamycin derivative. The following co-pending applications are incorporated herein by reference since each discloses thienamycin derivatives which may be used as starting materials in the preparation of the compound of the present invention. As mentioned above, this is one of the preferred processes of the present invention when R' is other than hydrogen and/or XR is other than OH. Incorporated by reference applications are: United States Patent Application Ser. Nos.: 634,291; 634,295; 634,298; 634,006; and 634,294 all filed Nov. 21, 1975 each now abandoned respectively of United States Patent Application Ser. Nos. 733,653, 733,613, 733,651, 733,655 and 733,652, all filed Oct. 18, 1976, each now abandoned respectively in favor of United States Patent Application Ser. Nos. 861,247, 861,150, 861,314, 861,234 and 861,246, all filed Dec. 16, 1977.

Incorporated by reference Patent Application Ser. No. 634,291 (filed Nov. 21, 1975) discloses N-acyl derivatives of thienamycin. As discussed above, such N-acyl thienamycin derivatives, particularly those wherein the acyl moiety comprises an aromatic nucleus, are preferred starting materials in the practice of the present invention.

Incorporated by reference, United States Patent Application Ser. No. 634,295 (filed Nov. 21, 1975) discloses and claims N- and carboxyl derivatives of thienamycin:

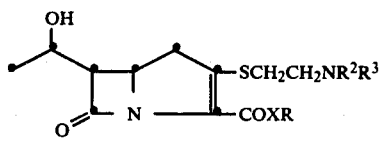

wherein R² and R³ are selected from the group consisting of hydrogen and acyl (the term "acyl" having been defined above) and X and R are as defined above. Such N- and carboxyl thienamycin derivatives are useful as starting materials in the preparation of embodiments of the present invention wherein the carboxyl group is derivatized as indicated.

Incorporated by reference, United States Patent Application Ser. No. 634,298 (filed Nov. 21, 1975) describes and claims carboxyl derivatives of thienamycin wherein the carboxyl function, —COXR, is as defined above. Such derivatives are useful as starting materials in the practice of the present invention when it is desired to obtain embodiments of the present invention wherein the carboxyl function is derivatized as described.

Incorporated by reference, United States Patent Application Ser. No. 634,006 (filed Nov. 21, 1975) describes and claims O- derivatives of thienamycin:

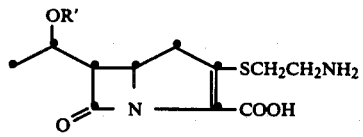

wherein R' is as defined above. Such O- thienamycin derivatives are useful as starting materials in the practice of the present invention for the preparation of embodiments of the present invention wherein the secondary alcohol group is derivatized as shows.

Incorporated by reference, United States Patent Application Ser. No. 634,294 (filed Nov. 21, 1975) describes and claims O-, N- and carboxyl derivatives of thienamycin:

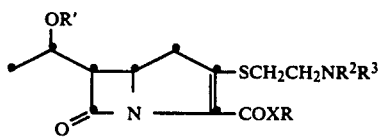

wherein R', X, R, R² and R³ are as defined above. Such trisubstituted thienamycin derivatives are useful in the preparation of embodiments of the present invention wherein the carboxyl and secondary alcohol groups are derivatized as shown.

Alternatively, operating upon the basic nucleus (Ia) the derivatized embodiments of the present invention are obtained according to the following reaction scheme:

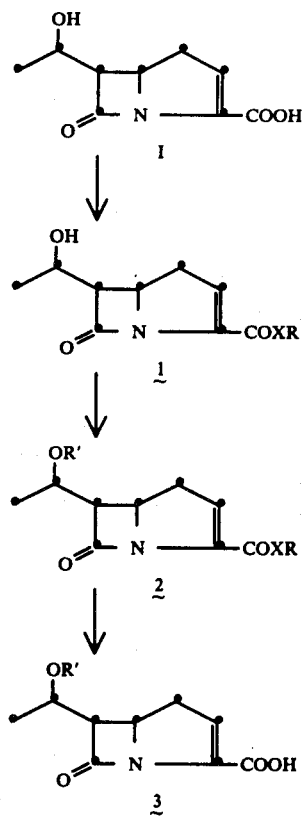

wherein X, R and R' are as previously defined.

In words relative to the above reaction diagram, derivatization of the carboxyl group is preferably conducted first followed, when desired, by derivatization of the secondary alcohol (e.g., 1→2). When it is desired to obtain embodiments denoted by 3, it is preferred that X be oxygen and that R be selected from the easily removable carboxyl blocking or protecting groups which are disclosed above; this transformation, 2→3, is executed by hydrolysis or hydrogenation according to procedures well known in the art for the removal of the carboxyl protecting groups.

Relative to the transformation of the basic nucelus I, to the embodiment designated as 1 above, it is to be noted that the transformation is effected by conventional procedures known in the art. Such procedures (I→1) include:

(1.) Reaction of the free acid (I) with a diazoalkane such as diazomethane, phenyldiazomethane, diphenyldiazomethane and the like in an inert solvent such as dioxane, THF, halohydrocarbons, acetonitrile, ethylacetate, and the like at a temperature of from −78° C., to 25° C., for from a few minutes to 2 hours.

(2.) Reaction of the metallic salts (e.g., Na, Li) of the acid (I) with an activated alkyl halide such as methyliodide, benzylbromide, or m-phenoxybenzylbromide, p-t-butylbenzylbromide, m-phenoxybenzylbromide, and the like. Suitable reaction conditions include inert, anhydrous polar non-protic solvents such as hexamethylphosphoramide, DMF, dimethylsulfoxide (DMSO), THF, dioxane, and the like at a temperature of from 20° C., to 60° C., for from a few minutes to 4 hours.

(3.) Reaction of the free acid (I) with an alcohol such as methanol, ethanol, benzyl alcohol, and the like. This reaction may be conducted in the presence of a carbodiimide condensing agent such as dicyclohexylcarbodiimide or the like. Suitable solvents, at a temperature of from 0° C. to reflux for from 15 minutes to 18 hours, include $CHCl_3$, $CCl_4$, $CH_2Cl_2$ and the like.

(4.) Reaction of an acid anhydride of I, prepared by reacting the free acid (I) with an acid chloride such as ethylchloroformate, benzylchloroformate and the like, with an alcohol such as those listed in (3.) under the same conditions of reaction as given above for (3.). The anhydride is prepared by reacting I and the acid chloride in a solvent such as tetrahydrofuran (THF), $CH_2Cl_2$ and the like at a temperature of from $-20°$ C. to reflux for from 5 minutes to 2 hours.

(5.) Reaction of labile esters of I such as the trimethylsilyl ester, dimethyl-t-butylsilyl ester or the like with RX' wherein X' is halogen such as bromo and chloro and R is as defined in a solvent such as THF, $CH_2Cl_2$ and the like at a temperature of from 0° C. to reflux for from 15 minutes to 16 hours in the presence of a base such as triethylamine, pyridine and the like. Such trialkylsilyl esters of the carboxyl group, for example the trimethylsilyl ester, are conveniently prepared by treating I with an excess of hexamethyldisilazane and a stoichiometric amount of trimethylchlorosilane at 25° C., with vigorous stirring under a $N_2$ atmosphere. The resulting $NH_4Cl$ is removed by centrifugation and the solvent is removed by evaporation to provide the desired silyl ester.

The amides of the present invnetion are most conveniently prepared by reacting the acid anhydride of I with ammonia or with the amine of choice, e.g., the alkyl-, dialkyl-, aralkyl- or heterocyclic amines listed above.

The above-recited schemes of esterification are well-known in the related bicyclic β-lactam antibiotic art and indeed in all of general organic synthesis and it is to be noted that there is no undue criticality of reaction parameters in the preparation of the compounds of the present invention.

Derivatization of the secondary alcoholic group to provide embodiments of the present invention designated as 2 and 3 in the above reaction scheme is accomplished by any of a variety of well-known esterification or etherification reactions upon the secondary alcoholic group of I in its carboxyl protected form, (1→2). Such procedures (1→2) include:

(1.) For the preparation of ether embodiments of the present invention, the acid catalized reaction of 1. with a diazoalkane such as diazomethane, phenyldiazomethane, diphenyldiazomethane and the like in an inert solvent such as dioxane, tetrahydrofuran (THF), halohydrocarbons such as $CH_2Cl_2$, ethylacetate and the like in the presence of a catalytic amount of a strong acid or Lewis acid such as toluenesulfonic acid, trifluoroacetic acid, fluoboric acid, boron trifluoride and the like at a temperature of from $-78°$ C. to 25° C. for from a few minutes to 2 hours;

(2.) For the preparation of ether embodiments of the present invention, the reaction of 1 with an activated halide such as methyliodide, benzylbromide, m-phenoxybenzylbromide and the like in the presence of a strong base capable of forming the alcoholate anion of 1; suitable bases include alkali and alkaline earth metal oxides and hydrous oxides, alkali metal alkoxides such as potassium tertiary-butoxide, tertiary amines such as triethylamine, alkali metal alkyls and aryls such as phenyllithium, and alkali metal amides such as sodium amide; suitable solvents include any inert anhydrous solvent such as t-butanol, dimethylformamide (DMF), THF, hexmethylphosphoramide (HMPA) dioxane and the like at a temperature of from $-78°$ C. to 25° C., for from a few minutes to 4 hours;

(3.) For the preparation of ester embodiments, of the present invention, the reaction of 1 with any of the above-listed acyl radicals in their acid form; this reaction may be conducted in the presence of a carbodiimide condensing agent such as dicyclohexylcarbodiimide or the like; suitable solvents include any inert solvent such as $CHCl_3$, $CH_2Cl_2$ DMF, DMSO, HMPA, acetone, dioxane and the like at a temperature of from 0° C. to 60° C. for from 15 minutes to 12 hours;

(4.) For the preparation of ester embodiments of the present invention, the reaction of 1 with an acyl halide or an acid anhydride (wherein the acyl moiety is described above)—generally, when the above-described acylating reaction employs an acyl halide (suitabie halides are chloro, iodo, or bromo or acid anhydride) the reaction is conducted in an anhydrous organic solvent such as acetone, dioxane, methylenechloride chloroform, DMF, or the like in the presence of a suitable acceptor base such as $NaHCO_3$, MgO, triethylamine, pyridine, and the like at a temperature of from 0° C. to 40° C. for from 1 to 4 hours; suitable acyl halides and anhydrides include: acetic anhydride, bromoacetic anhydride, propionic anhydride, benzoylchloride, phenylacetyl chloride, azidoacetyl chloride, 2-thienylacetyl chloride, 2-, 3- and 4-nicotinyl chloride, p-nitrobenzoyl chloride, 2,6-dimethoxybenzoyl chloride, 4-guanidinophenylacetyl chloride, hydrochloride, methanesulfonyl chloride, dibenzylphosphorochloridate, dimethylthiophosphorochloridate, 2-furoyl ethyl, 2-furoyl ethyl carbonic anhydride, methylchloroformate, bis (p-nitrobenzyl)phosphorochloridate and the like;

(5.) For the preparation of ester embodiments of the present invention, the reaction of 1 with a suitably substituted ketene of isocyanate such as ketone, dimethyl ketone, methylisocyanate, methylisothiocyanate, chlorosulfonyl isocyanate and the like; suitable solvents include dioxane, tetrahydrofuran, chloroform and the like at a temperature of from $-70°$ C. to 60° C. for from 15 minutes to 18 hours.

The compounds of the present invention are valuable antibiotics active against various gram-positive and gram-negative bacteria and, accordingly, find utility in human and veterinary medicine and in inanimate systems. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus*. The antibacterial compounds of the invention may further be utilized as additives to animal feedstuffs for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as the active ingredient in any one of a variety of pharmaceutical preparations. These antibiotics and their corresponding pharmaceutically acceptable salt, ester and amide derivatives may be employed in capsule form or as tablets, powders or liquid solutions or as suspensions or elixirs. They may be adminstered orally, intravenously or intramuscularly. Such pharmaceutically acceptable forms include salts of the free amino group of the compounds of the present invention such as the phosphate, chloride and citrate, as well as salts, esters and amides of appropriate functional groups carrier by the substitutents R or R'. Such pharmaceutically acceptable forms are prepared according to procedures well-known in the art.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silica; disintegrants, for example potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops. Topical applications may be formulated in hydrophobic or hydrophilic bases as ointments, creams, lotions, paints, or powders.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intramammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg. of active ingredient per kg. of body weight.

The instant compositions may be administered in several unit dosage forms as, for example, in solid or liquid orally ingestible dosage form. The compositions per unit dosage, whether liquid or solid may contain from 0.1 to about 99% of active material, the preferred range being from about 10–60%. The compositions will generally contain from about 15 mg. to about 1500 mg. of the active ingredient; however, in general, it is preferable to employ a dosage amount in the range of from about 250 mg. to 1000 mg. In parenteral administration the unit dosage is usually the pure compounds in a slightly acidified sterile water solution or as the form of a soluble powder intended for solution.

The following examples further illustrate, but do not limit the product, process, compositional or method of treatment aspects of the present invention.

EXAMPLE 1

Sodium 6-($\alpha$-Hydroxyethyl)-7-oxo-1-azabicyclo[3.2.0]hept-2-ene-2-carboxylate from hydrogenolysis of N-phenoxyacetyl thienamycin sodium salt Step A. Preparation of N-phenoxyacetyl thienamycin sodium salt To a 250 ml flask containing thienamycin (190 mg) is added 30 ml of water, 0.6 g of sodium bicarbonate and 30 ml of dioxane. While the mixture is stirred and kept at 0° C., phenoxyacetyl chloride (170 mg) is added dropwise to the flask during a period of 10 minutes. The solution is stirred for an additional 10 minutes and then acidified with 30% phosphoric acid to pH 4.5. The acidified solution is quickly extracted with 50 ml of ether to remove excess reagent and its hydrolyzed product, phenoxyacetic acid. The aqueous layer so obtained is further acidified with 30% phosphoric acid to pH 2.0, and extracted with 50 ml of ethylacetate. The organic layer which contains the free acid of N-phenoxyacetyl thienamycin is separated and back extracted with 30 ml of aqueous solution containing 60 mg of sodium bicarbonate. The aqueous layer is freeze dried to yield 120 mg of N-phenoxyacetyl thienamycin sodium salt. Electrophoresis (0.5 M, pH 7.0, phosphate buffer, 2 KV for 20 min): single bioactive zone which moves 45 mm toward anode. UV: $\lambda_{max}^{H_2O}$ 302 nm.

Step B. Preparation of Sodium 6-($\alpha$-Hydroxyethyl)-7-oxo-1-azabicyclo[3.2.0]hept-2-ene-2-carboxylate To a 250 ml. hydrogenation flask containing 1.4 g of palladium oxide and 5 ml. of water is added 73 mg. of N-phenoxyacetyl thienamycin sodium salt in 27 ml. of water. The mixture is stirred under 1 atm hydrogen at 25° C. for 3 hours; whereupon the catalyst is removed by filtration. The filtrate is concentrated to 5 ml. and charged to a 80 ml. XAD-2 resin column. The column is eluted with water in 3 ml. fractions which are monitored by uv absorption. The fractions containing the title compound are identified, combined and freeze dried to give 12 mg. of sodium 6-(α-hydroxyethyl)-7-oxo-1-azabicyclo[3.2.0]hept-2-ene-2-carboxylate. Electrophoresis (0.5 M pH 7.0 phosphate buffer, 2 kv for 20 min): single bioactive zone which moves 70 mm toward anode. UV: $\lambda_{max}^{H2O}$ 265 nm. 100 MHZ NMR(D$_2$O): 1.29(d), 2.86(m), 3.39(q), 4.24(quintet), 4.26(dt) and 6.27 ppm(q). The antibacterial activity of this compound is inhibited by β-lactamase.

EXAMPLE 2

Sodium 6-(α-Hydroxyethyl)-7-oxo-1-azabicyclo[3.2.0]hept-2-ene-2-carboxylate from hydrogenolysis of thienamycin sodium salt Following the procedure of Example 1, Step B, except that the N-phenoxyacetyl thienamycin is replaced by an equivalent amount of thienamycin there is obtained the tile compound which is isolated from the reaction mixture by preparative thin layer chromatography using 20% methanol in water as the eluting solvent on silica gel plates (silica gel GF, Analtech Inc.)

EXAMPLE 3

Following the procedure of Example 1, Step B, the compounds illustrated in Table I below are obtained when the N-phenoxyacetyl thienamycin substrate of Example 1 (Step B) is replaced by an equivalent amount of the corresponding thienamycin derivatives necessary to provide the product illustrated in the table. Exceptions to the established procedure are noted where necessary in the column labelled "Remarks":

TABLE I

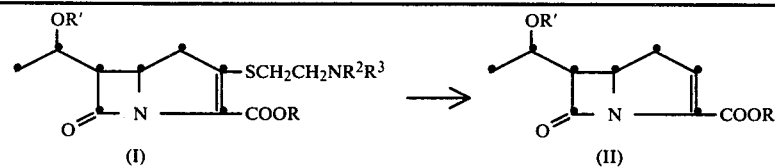

| Product (II) | | Starting Material (I) | | | | |
|---|---|---|---|---|---|---|
| R | R' | R | R' | R² | R³ | Remarks |
| Na | H | Na | H | H | COCH$_3$ | |
| Na | H | Na | H | H | COCH$_2$Br | |
| Na | H | Na | H | H | COCH$_2$N$_3$ | |
| Na | H | Na | H | H | COCH$_2$CH$_2$N$_3$ | |
| Na | H | Na | H | H | COCH$_2$CH$_2$Br | |
| Na | H | Na | H | H | COC$_6$H$_5$ | Platinum oxide catalyst replaces palladium oxide |
| Na | H | Na | H | H | COCH$_2$C$_6$H$_5$ | Platinum oxide catalyst replaces palladium oxide |
| Na | H | Na | H | H | CO$_2$CH$_2$C$_6$H$_5$ | Platinum oxide catalyst replaces palladium oxide |
| Na | H | Na | H | H | CO$_2$CH$_2$C$_6$H$_4$-p-NO$_2$ | Platinum oxide catalyst replaces palladium oxide |
| Na | H | Na | H | H | CO$_2$CH$_2$C$_6$H$_4$-o-NO$_2$ | Platinum oxide catalyst replaces palladium oxide |
| Na | H | Na | H | H | CH$_2$C$_6$H$_5$ | Platinum oxide catalyst replaces palladium oxide |
| Na | H | Na | H | H | −C(=NH)H | Platinum oxide catalyst replaces palladium oxide |
| Na | COCH$_3$ | CH$_2$C$_6$H$_5$ | COCH$_3$ | H | COCH$_2$OC$_6$H$_5$ | 1:1(vol.)Dioxane:Aqueous phosphate buffer (0.1M, pH 7.0) as solvent |
| Na | COCH$_3$ | CH$_2$(C$_6$H$_4$)-p-NO$_2$ | COCH$_3$ | H | COCH$_2$OC$_6$H$_5$ | 1:1(vol.)Dioxane:Aqueous phosphate buffer (0.1M, pH 7.0) as solvent |
| Na | CH$_3$ | CH$_2$(C$_6$H$_4$)-p-NO$_2$ | CH$_3$ | H | COCH$_2$OC$_6$H$_5$ | 1:1(vol.)Dioxane:Aqueous phosphate buffer (0.1M, pH 7.0) as solvent |

TABLE I-continued $$\text{(I)} \longrightarrow \text{(II)}$$

Structure (I): β-lactam with OR' substituent, SCH$_2$CH$_2$NR$^2$R$^3$ and COOR groups
Structure (II): β-lactam product with OR' and COOR groups

| Product (II) | | Starting Material (I) | | | | Remarks |
|---|---|---|---|---|---|---|
| R | R' | R | R' | R$^2$ | R$^3$ | |
| Na | CO$_2$Et | CH$_2$(C$_6$H$_4$)-p-NO$_2$ | CO$_2$Et | H | COCH$_2$OC$_6$H$_5$ | 1:1(vol.)Dioxane:Aqueous phosphate buffer (0.1M, pH 7.0) as solvent |
| Na | C$_6$H$_5$ | CH$_2$(C$_6$H$_4$)-p-NO$_2$ | C$_6$H$_5$ | H | COCH$_2$OC$_6$H$_5$ | 1:1(vol.)Dioxane:Aqueous phosphate buffer (0.1M, pH 7.0) as solvent |
| Na | CO$_2$N(C$_6$H$_5$)$_2$ | CH$_2$(C$_6$H$_4$)-p-NO$_2$ | CO$_2$N(C$_6$H$_5$)$_2$ | H | COCH$_2$OC$_6$H$_5$ | 1:1(vol.)Dioxane:Aqueous phosphate buffer (0.1M, pH 7.0) as solvent |
| Na | PO(OMe)$_2$ | CH$_2$(C$_6$H$_4$)-p-NO$_2$ | PO(OMe)$_2$ | H | COCH$_2$OC$_6$H$_5$ | 1:1(vol.)Dioxane:Aqueous phosphate buffer (0.1M, pH 7.0) as solvent |
| Na | PO[N(CH$_3$)$_2$]$_2$ | CH$_2$(C$_6$H$_4$)-p-NO$_2$ | PO(OMe$_2$)$_2$ | H | COCH$_2$OC$_6$H$_5$ | 1:1(vol.)Dioxane:Aqueous phosphate buffer (0.1M, pH 7.0) as solvent |
| Na | PS(OMe)$_2$ | CH$_2$(C$_6$H$_4$)-p-NO$_2$ | PS(OMe)$_2$ | H | COCH$_2$OC$_6$H$_5$ | 1:1(vol.)Dioxane:Aqueous phosphate buffer (0.1M, pH 7.0) as solvent |
| Na | PS[N(CH$_3$)$_2$]$_2$ | CH$_2$(C$_6$H$_4$)-p-NO$_2$ | PS(NMe$_2$)$_2$ | H | COCH$_2$OC$_6$H$_5$ | 1:1(vol.)Dioxane:Aqueous phosphate buffer (0.1M, pH 7.0) as solvent |
| CH$_2$OC(O)C(CH$_3$)$_3$ | COCH$_3$ | CH$_2$OC(O)CMe$_3$ | COCH$_3$ | H | COCH$_2$OC$_6$H$_5$ | (1) ethylacetate as solvent, (2) product isolated by TLC on silica gel with ethyl acetate as solvent |
| CH$_2$OC(O)CMe$_3$ | CH$_3$ | CH$_2$OC(O)CMe$_3$ | CH$_3$ | H | COCH$_2$OC$_6$H$_5$ | (1) ethylacetate as solvent, (2) product isolated by TLC on silica gel with ethyl acetate as solvent |
| CH$_2$-C$_6$H$_4$-CMe$_3$ | CO$_2$Et | CH$_2$-C$_6$H$_4$-CMe$_3$ | CO$_2$Et | H | COCH$_2$OC$_6$H$_5$ | (1) ethylacetate as solvent, (2) product isolated by TLC on silica gel with ethyl acetate as solvent |
| CH$_3$ | COCH$_3$ | CH$_3$ | COCH$_3$ | H | COCH$_2$OC$_6$H$_5$ | (1) ethylacetate as solvent, (2) product isolated by TLC on silica gel with ethyl acetate as |

TABLE I-continued

| Product (II) | | Starting Material (I) | | | | |
|---|---|---|---|---|---|---|
| R | R' | R | R' | R² | R³ | Remarks |
| | | | | | | solvent |

Me = CH₃
Et = C₂H₅

EXAMPLE 4

Preparation of Benzyl 6-(α-Hydroxyethy)-7-oxo-1-azabicyclo[3.2.0]-hept-2-ene-2-carboxylate (II)

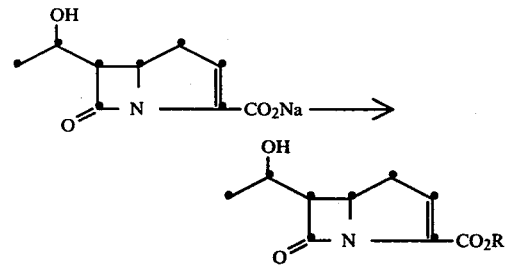

R = CH₂C₆H₅

Sodium 6-(α-hydroxyethyl)-7-oxo-1-azabicyclo[3.2.0]-hept-2-ene-2-carboxylate (I) (5 mg) is stirred with benzylbromide (0.2 ml) in hexamethylphosphoramide (0.5 ml) at 25° C. for 30 min. To the mixture is added 5 ml. of ethyl acetate. After the mixture is thoroughly washed with water, the organic layer is separated, dried over sodium sulfate and concentrated to 0.2 ml. The desired product (3.0 mg) is isolated by TLC, silica gel GF plates ($R_f$ 0.31, 20% ethylacetate/chloroform). The product shows ir absorption at 1780 cm$^{-1}$ (β-lactam), uv absorption at 276 nm, mass spectrum at m/e 287 (molecular ion) and nmr resonance at 3.18 ppm (q, J=3.0 and 6.0 Hz); which data are consistent with the assigned structure (II, R=CH₂-C₆H₅).

EXAMPLE 5

Preparation of Benzyl 6-(α-Acetoxyethyl)-7-oxo-1-azabicyclo[3.2.0]-hept-2-ene-2-carboxylate (II)

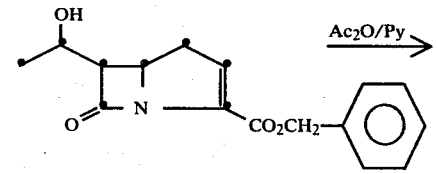

Benzyl 6-(α-Hydroxyethyl)-7-oxo-1-azabicyclo [3.2.0]hept-2-ene-2-carboxylate (I) (18 mg) is dissolved in 1 ml of pyridine (Py) and 0.2 ml of acetic anhydride (Ac₂O). The mixture is stirred at 25° C. for 3 hours and then evaporated to dryness to give oily residue. The residue is dissolved in 0.2 ml chloroform and chromatographed on two 20×20 cm, 250μ silica gel TLC plates ($R_f$ 0.56, 20% ethylacetate/chloroform) to give 4 mg. of the desired product (II) which shows nmr (CDCl₃, 60 MHZ) resonances at 2.02 (s, OAc), 6.48 (t, vinyl proton) and 7.40 ppm (m, aromatic protons) and ir (CHCl₃) carbonyl vibrations at 1780 (β-lactam) and 1740 cm$^{-1}$ (esters).

EXAMPLE 6

Preparation of sodium 6-(α-Acetoxyethyl)-7-oxo-1-azabicyclo[3.2.0]-hept-2-ene-2-carboxylate (II)

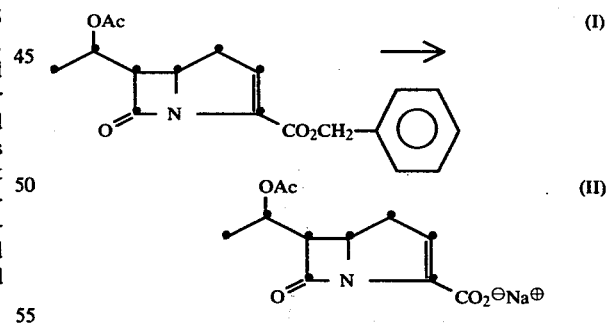

Benzyl 6-(α-Acetoxyethyl)-7-oxo-1-azabicyclo [3.2.0]-hept-2-ene-2-carboxylate (I) (4 mg) is dissolved in 2 ml of dioxane and 2 ml of phosphate buffer (0.1 M, pH 7.0). The mixture is stirred at 25° C. under 1 atm of hydrogen in the presence of 10% Pd/C catalyst (10 mg.) for 10 min. The mixture is then filtered from the catalyst and extracted with 5×2 ml ether. The aqueous layer is separated and freeze dried to give 1 mg of the title compound which is biologically active against Staphylococcus. The product shows uv absorption at 268 nm and HPLC retention time of 6.5 min as compared to that of 3.2 min for its 6-(α-hydroxy) analogue (2 ft.×⅛ in. C₁₈ Bondapak column eluted with 10% THF aqueous solution at a flow rate of 0.5 ml/min).

EXAMPLE 7

Following the procedure of Example 4 except that there is substituted for the benzylbromide of Example 4 an equivalent amount of bromomethylpivalate, 1-bromo-3-methyl-2-butene, 1-chloro-2-methylpropene, p-t-butylbenzyl bromide and 3-bromophthalide, there is obtained respectively, the following esters:

R pivaloyloxymethyl,
3-methyl-2-butene-1-yl,
2-methyl-2-propene-1-yl,
p-t-butyl benzyl, and phthalidyl.

EXAMPLE 8

Following the procedure of Example 5 except that there is substituted for the acetic anhydride/pyridine of Example 5 an equivalent amount of ethylchloroformate in the presence of an equivalent amount of triethylamine in the solvent methylene chloride; methyliodide in the presence of an equivalent amount of lithium diisopropylamide in the solvent dimethylformamide; methanesulfonylchloride in the presence of an equivalent amount of triethylamine in the solvent methylenechloride and dimethylphosphorochloridate in the presence of an equivalent amount of triethylamine in the solvent methylene chloride, respectively, there is obtained the following (O-R')- O-ethoxycarbonyl-, O-methyl-, O-methanesulfonyl-, and O-dimethoxyphosphinyl derivatives of benzyl 6-(α-hydroxyethyl)-7-oxo-1-azabicyclo[3.2.0]-hept-2-ene-2-carboxylate.

EXAMPLE 9

Following the procedure of Example 6 except that there is substituted for benzyl 6-(α-Acetoxyethyl)-7-oxo-1-azabicyclo[3.2.0]-hept-2-ene-2-carboxylate, an equivalent amount of O-ethoxycarbonyl, O-methyl, and O-dimethoxyphosphinyl derivatives of benzyl 6-(α-Hydroxyethyl)-7-oxo-1-azabicyclo[3.2.0]-hept-2-ene-2-carboxylate, there is obtained, respectively, the following compounds: O-ethyloxycarbonyl, O-methyl and O-dimethoxyphosphinyl derivatives of sodium 6-(α-hydroxyethyl)-7-oxo-1-azabicyclo [3.2.0]-hept-2-ene-2-carboxylate.

EXAMPLE 10

Preparation of Pharmaceutical Compositions

One such unit dosage form consists in mixing 120 mg. of pivaloyloxymethyl 6-(α-hydroxyethyl)-7-oxo-1-azabicyclo[3.2.0]hept-2-ene-2-carboxylate with 20 mg. of lactose and 5 mg of magnesium stearate and placing the 145 mg. mixture into a No. 3 gelatin capsule. Similarly, by employing more of the active ingredient and less lactose, other dosage forms can be put up in No. 3 gelatin capsules and should it be necessary to mix more than 145 mg. of ingredients together, larger capsules such as compressed tablets and pills can also be prepared. The following examples are illustrative of the preparation of pharmaceutical formulations:

| TABLET | PER TABLET |
| --- | --- |
| Pivaloyloxymethyl 6-(α-hydroxyethyl)-7-oxo-1-azabicyclo[3 . 2 . 0]hept-2-ene-2-carboxylate | 125 mg. |
| Cornstarch, U.S.P. | 6 mg. |
| Dicalcium Phosphate | 192 mg. |
| Lactose, U.S.P. | 190 mg. |

The active ingredient is blended with the dicalcium phosphate, lactose and about half of the cornstarch. The mixture is then granulated with a 15% cornstarch paste (6 mg.) and rough-screened. It is dried at 45° C. and screense again through No. 16 screens. The balance of the cornstarch and the magnesium stearate is added and the mixture is compressed into tablets, approximately 0.5 inch in diameter each weighing 800 mg.

| PARENTERAL SOLUTION | |
| --- | --- |
| Ampoule: | |
| Sodium 6-(α-hydroxyethyl)-7-oxo-1-azabicyclo[3 . 2 . 0]hept-2-ene-2-carboxylate | 500 mg. |
| Diluent: Serile Water for Injection | 2 cc. |
| OPTHALMIC SOLUTION | |
| Sodium 6-(α-hydroxyethyl)-7-oxo-1-azabicyclo[3 . 2 . 0]hept-2-ene-2-carboxylate | 100 mg. |
| Hydroxypropylmethyl Cellulose | 5 mg. |
| Sterile Water to | 1 ml. |
| OTIC SOLUTION | |
| Sodium 6-(α-hydroxyethyl)-7-oxo-1-azabicyclo[3 . 2 . 0]hept-2-ene-2-carboxylate | 100 mg. |
| Benzalkonium Chloride | 0.1 mg. |
| Sterile Water to | 1 ml. |
| TOPICAL OINTMENT | |
| Pivaloyloxymethyl 6-(α-hydroxyethyl)-7-oxo-1-azabicyclo[3 . 2 . 0]hept-2-ene-2-carboxylate | 100 mg. |
| Polyethylene Glycol 4000 U.S.P. | 400 mg. |
| Polyethylene Glycol 400 U.S.P. | 1.0 gram |

The active ingredient in the above formulations may be administered alone or in combination with other biologically active ingredients as, or example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

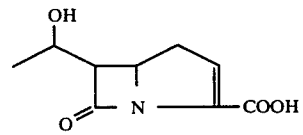

and the pharmaceutically acceptable salts thereof.

2. A compound having the structure:

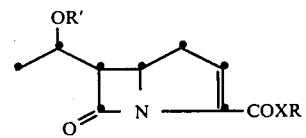

and the pharmaceutically acceptable salts thereof; wherein:

X is oxygen or sulphur;

R' is selected from the group consisting of: hydrogen, loweralkyl having from 1 to 6 carbon atoms, allyl, 2-methyl-2-propenyl, benzyl, p-bromobenzyl, p-t-butylbenzyl, alkylthioalkyl having from 2 to 8 carbon atoms; acyl having the general formula:

or

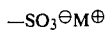

wherein: X' is oxygen or sulphur; $M^{\oplus}$ is hydrogen or an alkali metal cation and R" is selected from the group consisting of hydrogen, amino, mono- and dialkylamino wherein the alkyl moiety has 1 to 6 carbon atoms; loweralkyl having 1 to 6 carbon atoms, phenylthio, alkoxy having from 1 to 6 carbon atoms; phenoxy, benzyloxy, p-nitrobenzyloxy, phenyl, allyl, 2-methyl-2-propenyl, benzyl, halo- and perhaloalkyl having from 1 to 6 carbon atoms wherein the halogen is selected from the group consisting of chloro, fluoro, and bromo; and R is selected from the group consisting of hydrogen, alkyl having 1 to 6 carbon atoms; phenacyl, p-bromophenacyl, pivaloyloxymethyl, halo- and perhaloalkyl having 1 to 6 carbon atoms wherein the halogen is chloro, fluoro or bromo; alkenyl having from 2 to 6 carbon atoms; benzyl, benzhydryl, p-t-butylenzyl, p-bromobenzyl, phthalidyl, 5-indanylmethyl, phenyl, 5-indanyl, acetylthiomethyl, acetylthioethyl, pivaloylthiomethyl, alkylthioalkyl, having 2–6 carbon atoms; and X is oxygen.

3. A compound according to claim 2 wherein R' is selected from the group consisting of hydrogen, methyl, allyl, phenyl, benzyl, methylthiomethyl, formyl, sulfo acetyl, carbamoyl, bromoacetyl, ethoxycarbonyl, p-nitrobenzyloxycarbonyl;

X is oxygen;

R is selected from the group consisting of hydrogen, methyl, t-butyl, phenacyl, p-bromophenacyl; pivaloyloxymethyl, 2,2,2-trichloroethyl, allyl, 3-methyl-2-butenyl, 2-methyl-2-propenyl, benzyl, benzylhydryl, p-t-butylbenzyl, phthalidyl, phenyl, 5-indanyl, acetylthiomethyl, acetylthioethyl, pivaloylthiomethyl, methylthiomethyl.

4. An antibiotic pharmaceutical composition consisting essentially of, in unitary dosage form, a therapeutically effective amount of a compound according to claim 1 and a pharmaceutical carrier therefor.

* * * * *